United States Patent
Kawamata

(10) Patent No.: US 6,843,765 B2
(45) Date of Patent: Jan. 18, 2005

(54) APPARATUS FOR GENERATING COMPOSITE WAVE TO REACTION POINT

(76) Inventor: Shin'ichi Kawamata, 9-9, Minamiazabu 2-chome, Minato-ku, Tokyo (JP)

( * ) Notice: Subject to any disclaimer, the term of this patent is extended or adjusted under 35 U.S.C. 154(b) by 0 days.

(21) Appl. No.: 10/408,227

(22) Filed: Apr. 8, 2003

(65) Prior Publication Data

US 2003/0225310 A1 Dec. 4, 2003

(30) Foreign Application Priority Data

May 28, 2002 (JP) ........................................ 2002-153251

(51) Int. Cl.[7] ........................... A61M 21/00; A61N 1/00
(52) U.S. Cl. ........................................ 600/28; 607/115
(58) Field of Search ........................... 600/28, 547, 26, 600/554, 27, 372, 545, 548; 128/902, 905; 607/145, 72, 136, 2, 46, 76, 74, 115, 57, 58, 88, 62, 66, 63; 131/270; 606/32, 189; 63/14.1; 602/45; 381/380, 322, 371, 374; 331/78

(56) References Cited

U.S. PATENT DOCUMENTS

| | | | | |
|---|---|---|---|---|
| 2,986,140 A | * | 5/1961 | Gardner et al. ............... | 600/28 |
| 4,014,323 A | * | 3/1977 | Gilmer et al. ............... | 600/547 |
| 4,305,402 A | * | 12/1981 | Katims ........................ | 600/554 |
| 4,319,584 A | * | 3/1982 | McCall ........................ | 607/136 |
| 4,450,846 A | * | 5/1984 | McCall ........................ | 607/136 |
| 4,965,838 A | * | 10/1990 | Kamon et al. ............... | 381/380 |
| 4,966,164 A | * | 10/1990 | Colsen et al. ................ | 607/72 |
| 5,458,625 A | * | 10/1995 | Kendall ....................... | 607/46 |
| 5,514,175 A | * | 5/1996 | Kim et al. ................... | 607/136 |
| 5,800,503 A | * | 9/1998 | Edmark et al. ............. | 607/145 |
| 6,267,721 B1 | * | 7/2001 | Welles ......................... | 600/26 |
| 6,285,905 B1 | * | 9/2001 | Chiang et al. ................ | 607/2 |
| 6,393,319 B1 | * | 5/2002 | Bock et al. ................... | 607/2 |
| 6,409,655 B1 | * | 6/2002 | Wilson et al. ................ | 600/28 |

* cited by examiner

Primary Examiner—Samuel G. Gilbert
Assistant Examiner—Nikita R. Veniaminov
(74) Attorney, Agent, or Firm—Rabin & Berdo, P.C.

(57) ABSTRACT

In an apparatus of stimulating a reaction point of a human body by a certain frequency signal, where frequencies respectively matching with organs are different and the matching frequencies are different in accordance with conditions of disease, a signal generating portion constituted by a melody IC is provided, a switching device is turned on and off in correspondence to a relaxation rhythm signal output from the generating portion, and a signal is obtained from a secondary side of an output transformer in synchronous with the on and off operations, thereby making it possible to treat by a plurality of signals in a band of a plurality of frequencies.

4 Claims, 2 Drawing Sheets

US 6,843,765 B2

APPARATUS FOR GENERATING COMPOSITE WAVE TO REACTION POINT

BACKGROUND OF THE INVENTION

Field of the Invention

The present invention relates to a composite wave generating apparatus by searching a reaction point, and more particularly to an apparatus for generating a composite wave to an ear reaction point in which a rhythm of music and a rhythm of electric potential vibration are interlocked with respect to an ear reaction point.

DESCRIPTION OF CONVENTIONAL ART

In accordance with an oriental medicine, it is known that a lot of reaction points (pressure points) exist in a human body and the reaction points respectively have specific effects. Further, corresponding reaction points connected to most of routes in organs and tissues of the human body are concentrated in an auricle or an ear holes. As described above, since an extremely large number of reaction points are concentrated in the ear, there has been proposed various kinds of stimulus apparatuses which treats various kinds of diseases by stimulating the reaction points in the ear.

For example, there is an apparatus which stimulates the reaction points by connecting a stimulus portion constituted by a clip to a weak electric current generator generating pulse signals and attaching the stimulus portion to the ear reaction points so as to flow a weak electric current such as a low frequency electric current or the like, thereby stimulating the reaction points to treat each of the organs and the tissues in the human body.

Further, there is another measure in which a headphone having a generator for generating sound signals from an external sound source in a center portion, and having a conductive pad to which electric signals having a specific waveform is supplied around the generator, is applied to the auricle, and these signals are transmitted to a central nerve such as a hypophysis or the like via a skin, thereby relieving a pain of a cancer and treating a geriatric disease.

The former structure listed up as the conventional art applies the electric current stimulus by mounting the stimulus portion to the specific reaction point within the auricle, however, since a lot of reaction points communicated with every organs and tissues of the human body via the routes are concentrated in the auricle, it is extremely hard to position the stimulus portions at a particular reaction point suitable to the case.

Further, in the case of making the patient listen to the music as in the latter, it is useful in the case that the listening patient shows an interest and reaches a tranquilizing state, however, functions of the organs and tissues are not activated even by stimulating the reaction points at a time when an automatic nerve is in an unbalance state, and accordingly, a sufficient treating effect can not be expected.

Further, it is commonly said in the conventionally proposed apparatuses including the both mentioned above that an outgoing frequency for stimulating the reaction point is manually set and the set frequency is a fixed frequency for at least a fixed time for treating once it is set. Even if the stimulus is repeated in accordance with the fixed frequency, it is impossible to sufficiently respond to the various organs and tissues having different matching frequencies.

That is, the reaction points concentrated in the auricle are respectively communicated with different organs and tissues via the routes, the treating frequencies matching with the respective organs and tissues are within a wide range between some hundreds Hz and some thousands Hz, and in addition, the matching frequencies are different in correspondence to conditions of the disease, and there is a problem that a sufficient treating effect can not be obtained by the fixed frequency.

SUMMARY OF THE INVENTION

The present invention is made by taking the points mentioned above into consideration, and an object of the present invention is to provide this kind of apparatus in which a treating efficiency and a relaxation effect given by a music are increased by supplying an electric potential vibration having a composite wave obtained by synchronizing a rhythm generated by a music with an electric potential frequency on a reaction point.

In accordance with a first aspect of the present invention, there is provided an apparatus of stimulating organs and tissues by supplying a pulse electric potential vibration to a reaction point of a human body comprising:

a melody generating portion for generating a previously stored melody signal in series with a power source;

a switching device having a control pole;

an output transformer; and a stimulus portion for activating the reaction point, wherein the control pole of the switching device is connected to an output terminal of the melody generating portion, the output transformer is connected in series with the switching device, a series circuit of the switching device and the output transformer is connected between positive and negative poles of the power source, and the stimulus portion is connected to a secondary coil of the output transformer via a jack and a plug.

In accordance with a second aspect of the present invention, there is provided an apparatus of generating a composite wave to a reaction point, wherein the stimulus portion connected to the secondary coil of the output transformer is an adapter for attaching to an auricle made of an electrically conductive material.

In accordance with a third aspect of the present invention, there is provided an apparatus of generating a composite wave to a reaction point, wherein the melody signal is a rhythm signal constituted by a frequency band between some hundreds Hz and some thousands Hz.

In accordance with a fourth aspect of the present invention, there is provided an apparatus of generating a composite wave to a reaction point, wherein an adjustment portion for adjusting an electric voltage is provided between the output terminal of the melody generating portion and the control pole of the switching device.

DESCRIPTION OF THE PREFERRED EMBODIMENT

Figure 1:
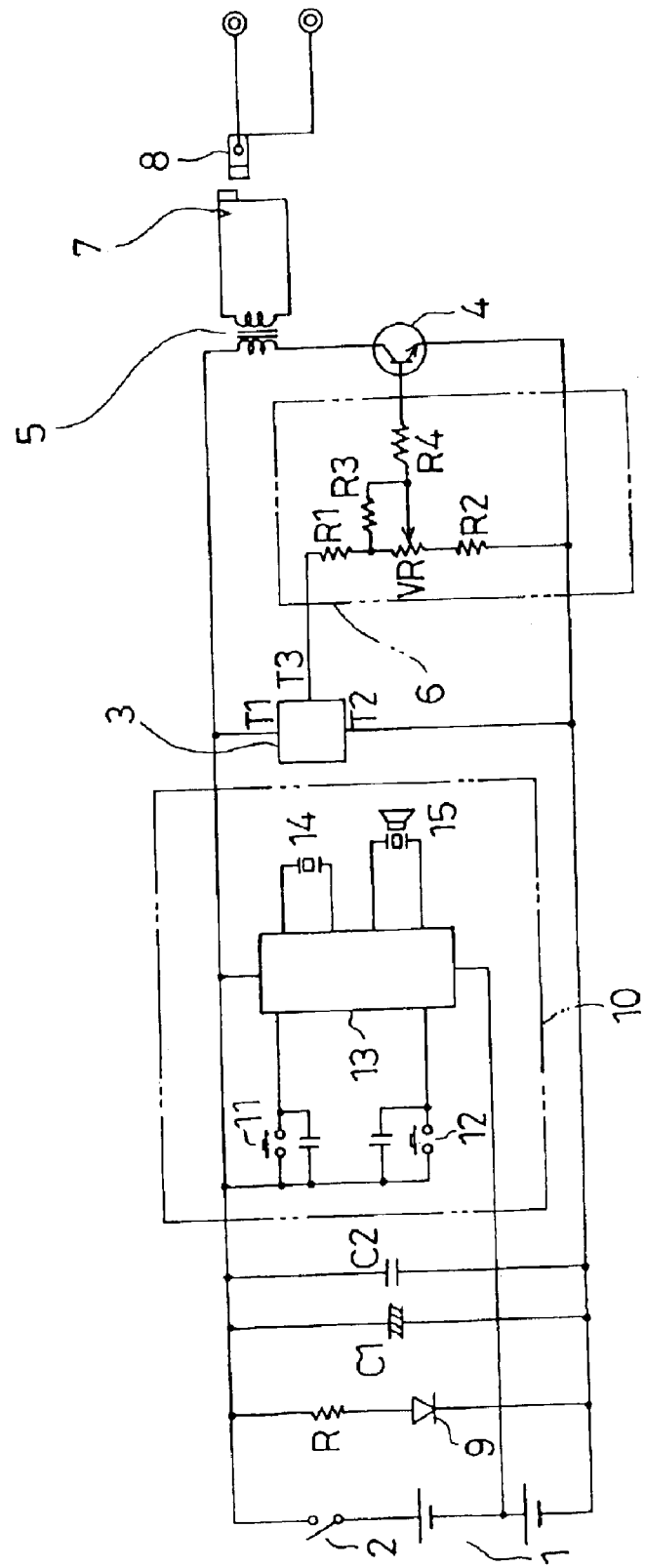
FIG. 1 is a schematic view showing an embodiment in accordance with the present invention.

FIG. 1 is a schematic view showing an embodiment in accordance with the present invention. Reference numeral 1 denotes a battery corresponding to a power source, reference numeral 2 denotes a power switch, and reference numeral 3 denotes a melody generating portion constituted by a melody IC. Terminals T1 and T2 of the melody generating portion 3 are connected in series with the power source 1 via the power switch 2. Signals for relaxation constituted by frequencies covering a sound range between some hundreds Hz and some thousands Hz are stored in the melody generating portion 3.

Reference numeral 4 denotes a switching device. A transistor is used for the switching device 4. One end of a primary coil of the output transformer 5 is connected to a collector of the transistor, and another end of the primary coil is connected to the terminal T1 of the melody generating portion 3. A jack 7 is connected to a secondary coil of the output transformer 5, and a plug 8 is inserted into the jack 7.

Further, an emitter of the transistor 4 is connected to a negative pole of the power source 1 together with the terminal T2 of the melody generating portion, and an output terminal T3 of the melody generating portion 3 is connected to a base (a control pole) of the transistor via a regulating portion 6. The regulating portion 6 is provided with a variable resistance VR and resistances R1 to R4 for adjusting, and a magnitude of a signal input to the base of the transistor 4 is regulated by changing a movable portion of the variable resistance VR.

Reference numeral 9 denotes a power source indicating lamp constituted by a light emitting diode or the like. A resistance R is connected in series with the power source indicating lamp and the power source indicating lamp indicates whether the power source is turned on or off. Reference symbols C1 and C2 denote a condenser.

Reference numeral 10 denotes a setting display portion, which is used for more increasing a function of the apparatus although not having a direct relation to the present invention. Reference numeral 11 denotes an operation mode setting switch, reference numeral 12 denotes a timer setting switch, and reference numeral 13 denotes a display portion in which a liquid crystal is used. Reference numeral 14 denotes a quartz oscillator constituting a communicator, and reference numeral 15 denotes a speaker.

Figure 2:
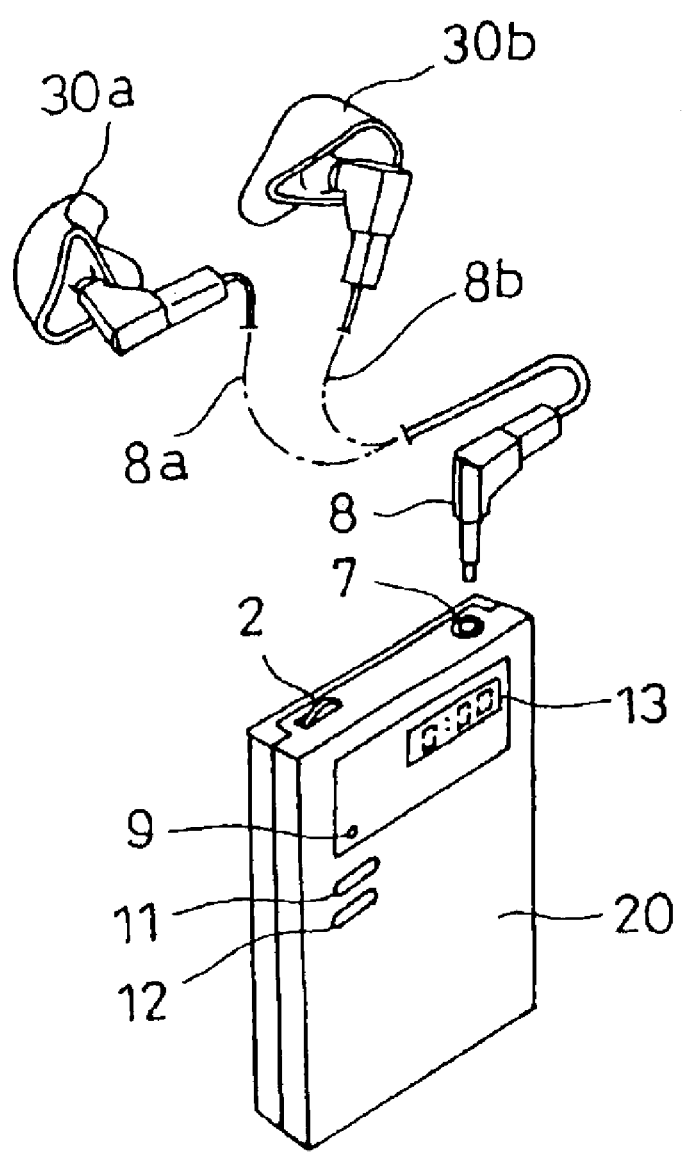
FIG. 2 is an outline view of the present invention.

FIG. 2 shows an outline portion of the present invention. An apparatus 20 is formed in a rectangular parallelepiped shape and has a size capable of being portably received in a pocket of a suit or the like. The power switch 2 is provided in one side of an upper end surface of the apparatus 20, and the jack 7 is mounted to another side. Further, the display portion 13, the switches 11 and 12 and the power source indicating lamp 9 are arranged in an upper portion of a surface of the apparatus.

A pair of leads 8a and 8b are connected to the plug 8 inserted and attached to the jack 7, and an adapter 30 (30a, 30b) corresponding to a stimulus portion attached to auricle portions in left and right ears and used for activating reaction points are respectively connected to leading ends of the respective leads. The adapters 30a and 30b are made electrically conductive by containing a metal conductive material of trace element in an elastic body, and have contact surfaces having a shape which substantially corresponds to the auricle portion for closely attaching to the auricle portion. That is, the contact surfaces of the adapters 30a and 30b are formed so as to be closely attached to the respective reaction points concentrated in the auricle portion.

In the apparatus structured in the manner mentioned above, a description will be given of an operation thereof.

When the adapters 30a and 30b are attached so that the contact surfaces are closely attached to the left and right auricles and the power switch 2 is turned on, the power source indicating lamp 9 is turned on, and the melody generating portion 3 starts an operation thereof. Since a melody rhythm signal having a frequency band for relaxation between some hundreds Hz and some thousands Hz is stored in the melody generating portion 3, a frequency signal having a pulse width and a pulse interval which correspond to the rhythm is output from an output terminal T3 in accordance with the start of the operation.

The signal output from the terminal T3 is divided into suitable signals by the regulating portion 6 and is applied to a gate of the switching device 4. Accordingly, the transistor corresponding to the switching device repeats on and off in correspondence to the pulse width and the pulse internal of the signal input to the base. When the transistor 4 is turned on, an electric current flows from the power source 1 in the primary coil of the output transformer 5 connected to the collector, and an electric voltage is induced in the secondary coil on the basis of a magnetic field caused by the electric current. This induced voltage means that an electric potential vibration of a composite wave is induced by turning on and off the transistor, that is, by the pulse signal corresponding to a melody signal of a music from the melody generating portion 3, and the electric potential vibration is supplied to the adapters 30a and 30b attached to the auricles via the jack 7 and the plug 8.

In this case, an electric resistance value of the reaction point in the auricle indicates a value about 400 kΩ in a normal state (in an active motion state), although there is a little difference in correspondence to the organs and the nerves, however, the value of resistance is changed such as 300 kΩ, 200 kΩ and 100 kΩ in correspondence to the degree under an inactive state. When the pulse signal is supplied to the adapters 30a and 30b mentioned above, an activation is started from the reaction point having the lowest value of resistance in the reaction points having the different values of resistance, thereby making a cure of the organs communicated with the reaction point, and since the electric potential vibration caused by the applied composite wave follows to the melody rhythm, a relaxation state is achieved.

In this case, in the above, the description is given only of the treatment with respect to the reaction point in the auricle, however, it goes without saying that a lot of reaction points exist in the other areas than the auricle, and the present invention can be applied to such the reaction points.

As described above, in accordance with the present invention, since the structure is made such that the electric potential vibration which is synchronized with the melody frequencies having a plurality of frequencies existing in a mixed manner is applied, it is not necessary to regulate the outgoing frequency per the reaction point as in the conventional art, and it is possible to cover all the reaction points having the frequencies in the melody frequency band.

Further, in the treatment, since the activation is started from the most inactive organ, it is possible to obtain an effective treatment effect by an automatic search even if the existence of the inactive organ is unclear.

What is claimed is:

1. An apparatus for generating a composite wave for activating organs and tissues by supplying a pulse electric potential vibration to a reaction point of a human body comprising:

a melody generating portion for generating a pulse signal having a pulse width and a pulse interval corresponding to a previously stored melody rhythm signal, the melody generating portion being connected in series with a power source;

a switching device having a control pole connected to an output terminal of the melody generating portion;

an output transformer connected in series with the switching device, the series combination thereof being connected between a positive pole and a negative pole of the power source; and at least one auricle adapter for insertion in an ear and connected to a secondary coil of the output transformer via a connector and made of an electrically conductive material, whereby the pulse electric potential is supplied to multiple reaction points within said ear and wherein said pulse electric potential corresponds to the previously stored melody rhythm signal and includes a plurality of frequencies.

2. An apparatus as claimed in claim 1, wherein said melody signal is a rhythm signal having frequencies within a frequency band between some hundreds Hz and some thousands Hz.

3. An apparatus as claimed in claim 2, further comprising an adjustment portion for adjusting an electric voltage coupled between the output terminal of said melody generating portion and the control pole of the switching device.

4. An apparatus as claimed in claim 1, further comprising an adjustment portion for adjusting an electric voltage coupled between the output terminal of said melody generating portion and the control pole of the switching device.

* * * * *